(12) United States Patent
Krauss et al.

(10) Patent No.: US 9,901,947 B2
(45) Date of Patent: *Feb. 27, 2018

(54) APPARATUS AND RELATED METHODS FOR DISPENSATION OF A LIQUID

(71) Applicant: Ingenierio, Inc., Fort Myers, FL (US)

(72) Inventors: Martin Krauss, Fort Myers, FL (US); Loo T. Yap, Fort Myers, FL (US)

(73) Assignee: INGENIERIO, INC., Fort Myers, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/230,769

(22) Filed: Aug. 8, 2016

(65) Prior Publication Data

US 2016/0346797 A1 Dec. 1, 2016

Related U.S. Application Data

(63) Continuation of application No. 13/924,135, filed on Jun. 21, 2013, now Pat. No. 9,433,959.

(51) Int. Cl.
| | |
|---|---|
| *B05B 11/02* | (2006.01) |
| *A61B 17/00* | (2006.01) |
| *B05B 1/34* | (2006.01) |
| *B05B 11/00* | (2006.01) |
| *A61M 15/00* | (2006.01) |

(52) U.S. Cl.
CPC ........ *B05B 11/02* (2013.01); *A61B 17/00491* (2013.01); *A61M 15/0001* (2014.02); *B05B 1/3436* (2013.01); *B05B 11/0054* (2013.01)

(58) Field of Classification Search
CPC .............. A61M 5/2455; A61M 5/2459; A61M 5/2466; A61M 15/0028; A61M 15/003; A61M 15/0031; A61M 15/0033; A61M 5/282; A61M 5/285; A61M 5/286; B05B 11/02; B05B 1/3436; B05B 11/0054; A61B 17/00491
USPC ........ 239/309, 320, 329, 330, 331, 80–83.5, 239/271, 272, 1
See application file for complete search history.

(56) References Cited

U.S. PATENT DOCUMENTS

| | | | | |
|---|---|---|---|---|
| 5,653,698 | A | * | 8/1997 | Niedospial ............ A61J 1/2096 604/403 |
| 2006/0178644 | A1 | * | 8/2006 | Reynolds .............. A61J 1/2093 604/232 |

(Continued)

*Primary Examiner* — Arthur O Hall
*Assistant Examiner* — Juan C Barrera
(74) *Attorney, Agent, or Firm* — Carole Patent Law Chtd.

(57) ABSTRACT

A dispenser apparatus is disclosed herein. A dispenser is disclosed herein. In various aspects, the dispenser includes a piston slidably sealingly engagable with a container containing a unit dose of liquid therein. The dispenser includes a cutting edge disposed about a piston face of the piston, the cutting edge configured to open a covering of rigid construction sealingly engaged with the container, in various aspects. A passage is formed between a piston face of the piston and a nozzle outlet of a nozzle to communicate fluid from the container through the nozzle outlet by sliding of the piston within the container, in various aspects. Methods of use of the dispenser are disclosed herein. This Abstract is presented to meet requirements of 37 C.F.R. §1.72(b) only. This Abstract is not intended to identify key elements of the apparatus and methods disclosed herein or to delineate the scope thereof.

16 Claims, 9 Drawing Sheets

(56) References Cited

U.S. PATENT DOCUMENTS

| | | | | |
|---|---|---|---|---|
| 2007/0270763 A1* | 11/2007 | Tanner | ............... | A61M 5/24 |
| | | | | 604/232 |
| 2009/0259195 A1* | 10/2009 | Lin Lee | ............ | A61M 5/24 |
| | | | | 604/195 |
| 2010/0108062 A1* | 5/2010 | Ganem | ......... | A61M 15/0028 |
| | | | | 128/203.21 |

* cited by examiner

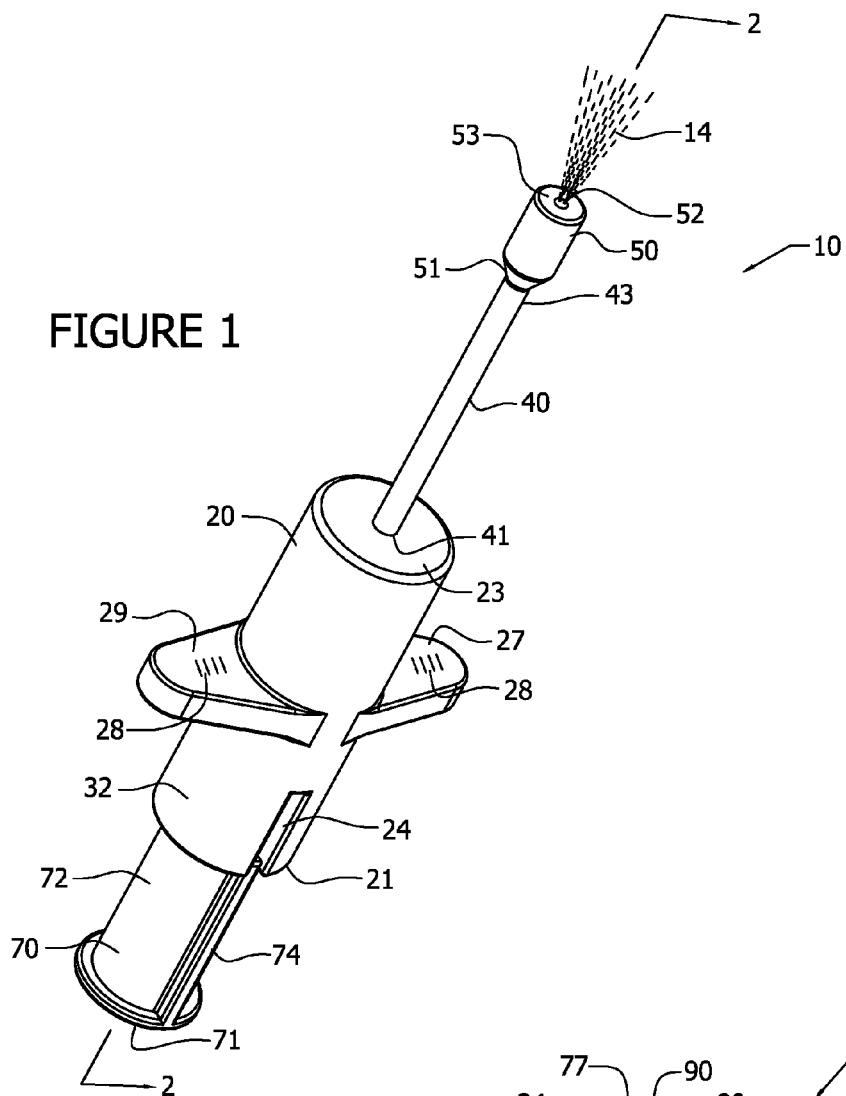
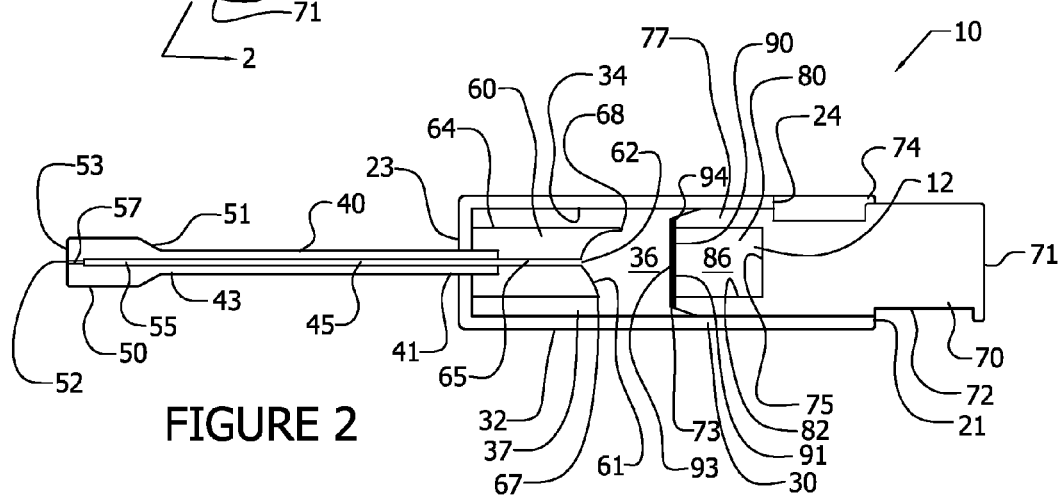

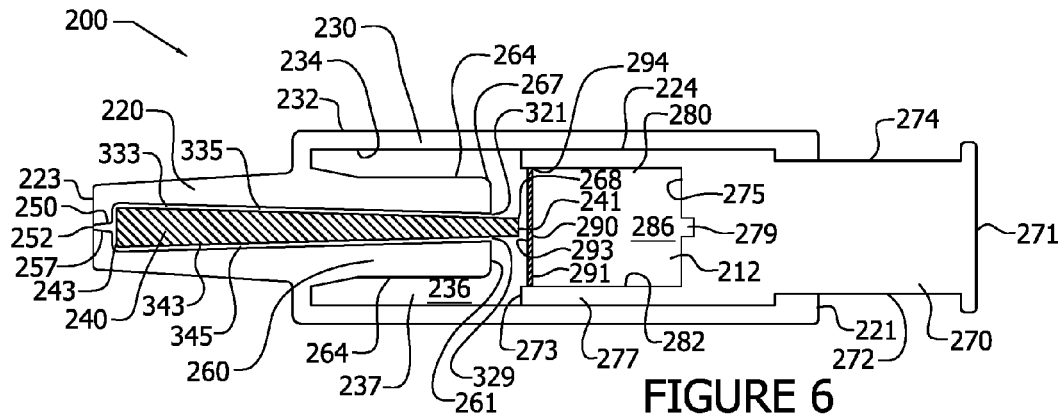
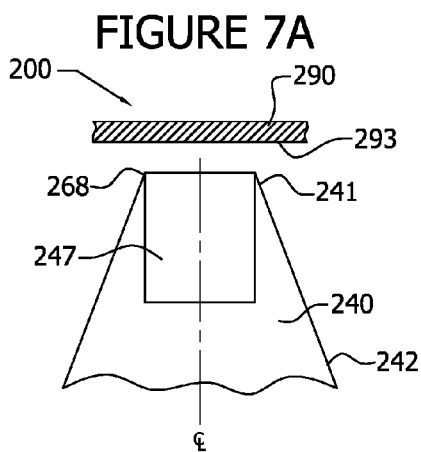
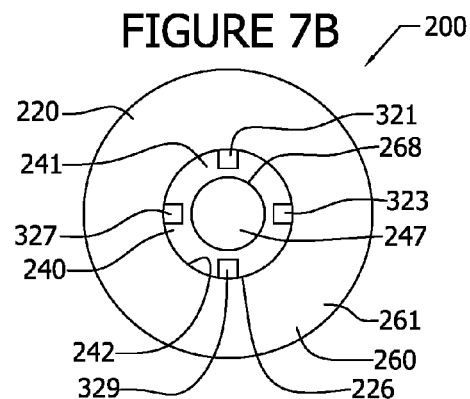
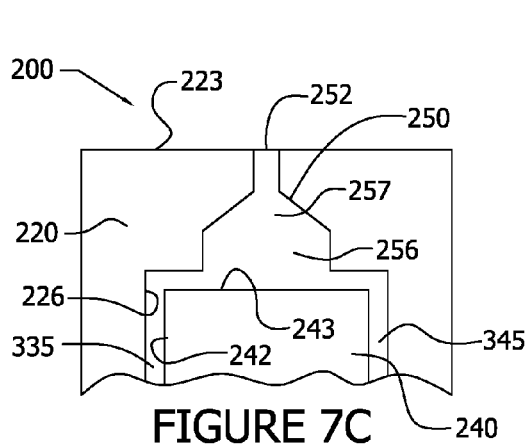
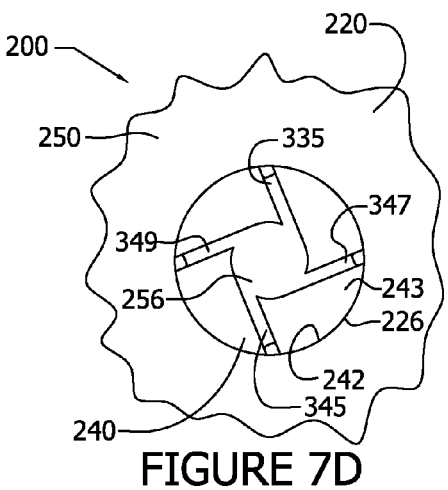

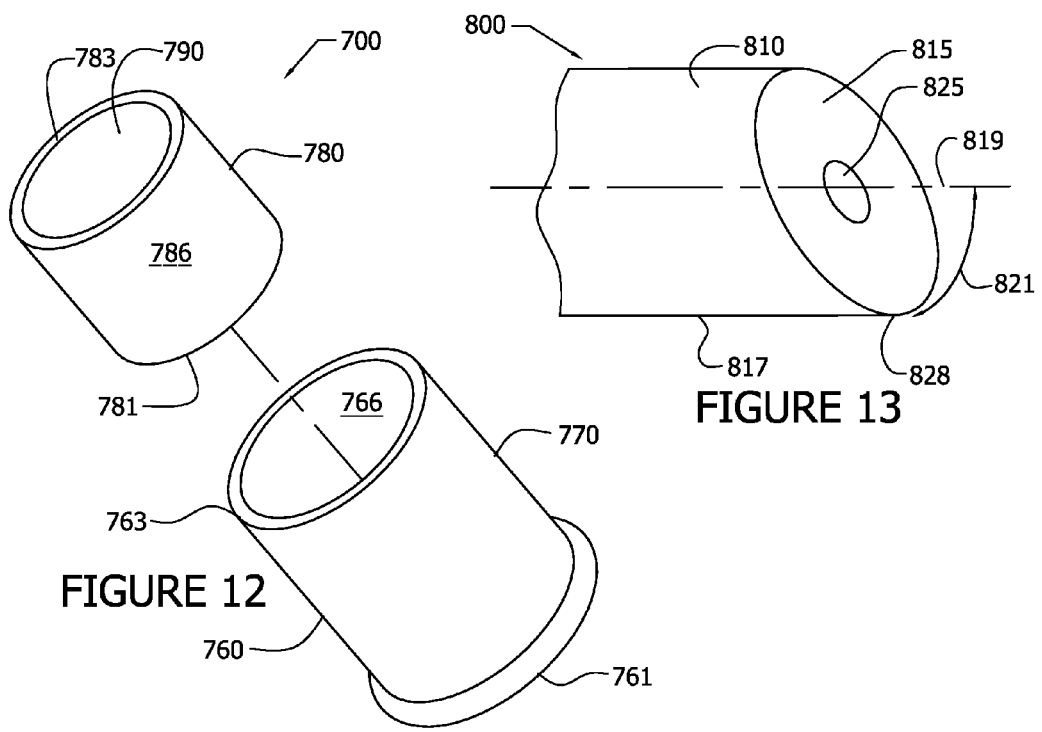
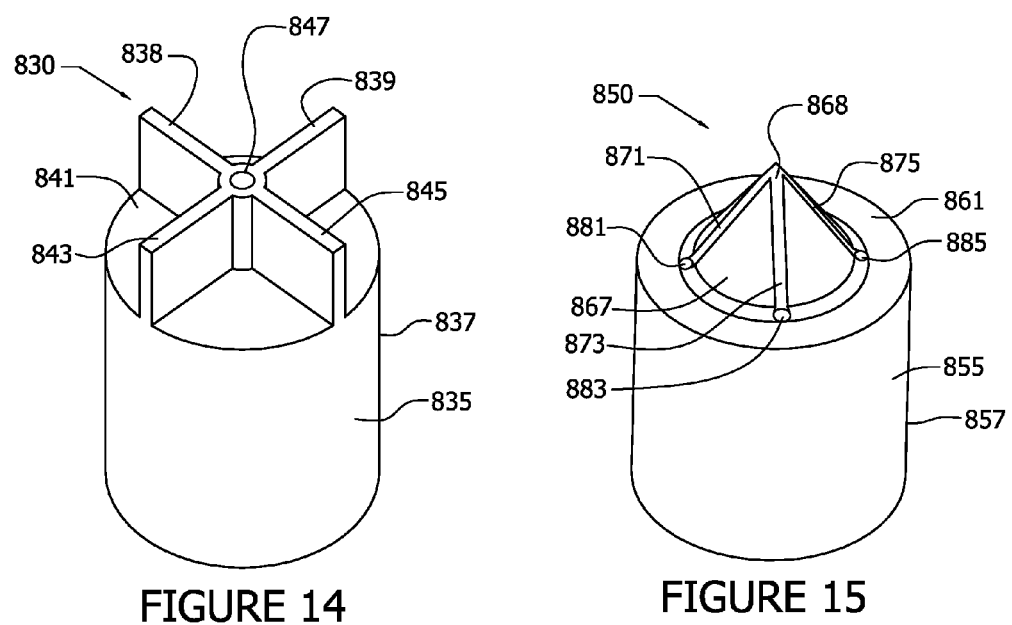

900 ─┐

Start ─ 901

↓

Insert container assembly into sleeve ─ 905

↓

Open Covering ─ 910

↓

Align piston with reservoir ─ 915

↓

Deliver unit dose of liquid as spray ─ 920

↓

End ─ 925

FIGURE 16

APPARATUS AND RELATED METHODS FOR DISPENSATION OF A LIQUID

CROSS-REFERENCE TO RELATED APPLICATIONS

The present application is a continuation of currently pending U.S. patent application Ser. No. 13/924,135 filed 21 Jun. 2013 and titled APPARATUS AND RELATED METHODS FOR DISPENSATION OF A LIQUID, which is hereby incorporated by reference in its entirety herein.

BACKGROUND

Field

The present disclosure relates to apparatus and related methods for spray dispensation of a liquid, and, more particularly, to apparatus and related methods for dispensation by spray of a unit dose of liquid from a hermetically sealed container.

Background

It may be desirable to dispense a unit dose of liquid by spray from a hermetically sealed container in various medical applications. Liquid, as used herein, includes, for example, various materials in the liquid phase, solutions, suspensions, and emulsions that may be required to be hermetically sealed from the environment until just prior to dispensing with precision in a controllable and reproducible manner. The liquid may be, for example, an adhesive for the closure of surgical incisions, attachment of tissues, the closure of cuts or wounds, such as a polymerizing or cross-linking medical adhesive. In various aspects, the liquid may be, for example, a disinfectant, an analgesic, an antibiotic, or other such medically useful liquid, as would be readily recognized by those of ordinary skill in the art upon study of the present disclosure. In various aspects, the liquid may be a liquid having use in medical, automotive, aerospace, marine, or any other applications in which a unit dose of liquid may be applied and wherein the liquid is hermetically sealed until dispensed. A unit dose refers an amount of the liquid desired to be available for dispensing. This amount may be the total amount required for one application, in some aspects. In other aspects, the unit dose may be an amount of liquid sufficient for multiple applications usable in one or more dispensing sessions.

The liquid may be hermetically sealed within a container to prevent exposure to the environment until dispensed. Hermetic seal and hermetically sealed, as used herein, means a seal that is impervious to air, gas, atomic clusters, molecular clusters, or particulates. The hermetic seal may conform to specific technical standards, in various aspects, and these standards may reflect various degrees of imperviousness to air, gas, atomic clusters, molecular clusters, or particulates. The hermetic sealing of the liquid within the container may, for example, prevent contamination of the liquid by various contaminants such as dust or microbes within the environment, may prevent degradation of the liquid by exposure to oxygen or other gasses in the atmosphere, or may prevent the loss of liquid from the container, the degradation of an evacuated container by leakage of air, gas, atomic clusters, molecular clusters, or particulates. into the container. As a further example, the hermetic sealing of the liquid within the container may prevent the escape of gas from the container, the gas, such as an inert gas, being included with the liquid within the container. The hermetic seal may prevent intrusion of bacteria, dirt or any other contaminants, or premature chemical or other reactions prior to dispensing, in various aspects.

Various devices have been developed for the spray dispensation of liquid from a hermetically sealed container. For example, one such device includes a breakable glass ampoule that contains the hermetically sealed liquid within. The ampoule is placed within a cavity formed within a flexible casing, so that breaking the ampoule causes the liquid to fill the cavity. Subsequent squeezing of the casing dispenses the liquid through a nozzle in fluid communication with the casing. However, the ampoule breaks in a random non-repeatable fashion that may contribute a measure of randomness to the dispensation of a unit dose of liquid by spray from the device. The breaking of the ampoule causes glass fragments to be suspended in the liquid. These glass fragments may block small passages formed in or about the nozzle, which may cause unpredictable variations in the spray delivered by the nozzle. Furthermore, the spray may contain glass fragments, which may be undesirable or even dangerous in a medical application.

Other devices either pressurize the liquid directly or indirectly through deforming container that contains the liquid. Deformation of the container causes a seal to rupture, with the liquid being dispensed following rupture of the seal. Such devices may be characterized by the randomness of the seal-rupturing process. The controllability of such devices may be compromised by the non-reproducible liquid pressure spike and flow spike directly following the rupture of the seal, which may make it difficult to deliver a unit dose of liquid by spray from such devices.

Yet another device requires a manual opening of the nozzle exit to unseal the initially hermetically sealed container and requires an inherently random squeezing of the container to dispense the liquid from through the nozzle from the container. This opening process presents impediments to designing appropriate nozzle systems. The randomness with which the container is squeezed may inhibit precise or predictable dispensation of a unit dose from the device.

Accordingly, there is a need for improved apparatus as well as related methods for dispensation by spray of a unit dose of liquid from a hermetically sealed container.

BRIEF SUMMARY OF THE INVENTION

These and other needs and disadvantages may be overcome by the apparatus and related manufactures and methods disclosed herein. Additional improvements and advantages may be recognized by those of ordinary skill in the art upon study of the present disclosure.

A dispenser is disclosed herein. In various aspects, the dispenser includes a piston slidably sealingly engagable with a container containing a unit dose of liquid therein. The dispenser includes a cutting edge disposed about a piston face of the piston, the cutting edge configured to open a covering of rigid construction sealingly engaged with the container, in various aspects. A passage is formed between a piston face of the piston and a nozzle outlet of a nozzle to communicate fluid from the container through the nozzle outlet by sliding of the piston within the container, in various aspects. Methods of use of the dispenser are disclosed herein.

This summary is presented to provide a basic understanding of some aspects of the apparatus and methods disclosed herein as a prelude to the detailed description that follows below. Accordingly, this summary is not intended to identify key elements of the apparatus and methods disclosed herein or to delineate the scope thereof.

BRIEF DESCRIPTION OF THE DRAWINGS

FIG. 1 illustrates by perspective view and exemplary implementation of a dispenser;

FIG. 2 illustrates by side cross-sectional view the exemplary implementation of the dispenser of FIG. 1;

FIG. 6 illustrates by side cross-sectional view another exemplary implementation of a dispenser;

FIG. 7A illustrates by side cross-sectional view portions of the exemplary implementation of the dispenser of FIG. 6;

FIG. 7B illustrates by top view portions of the exemplary implementation of the dispenser of FIG. 6;

FIG. 7C illustrates by side cross-sectional view portions of the exemplary implementation of the dispenser of FIG. 6;

FIG. 7D illustrates by frontal cross-sectional view portions of the exemplary implementation of the dispenser of FIG. 6;

FIG. 12 illustrates by exploded perspective view portions of another exemplary implementation of a dispenser;

FIG. 13 illustrates by perspective view portions of another exemplary implementation of a dispenser;

FIG. 14 illustrates by perspective view portions of another exemplary implementation of a dispenser;

FIG. 15 illustrates by perspective view portions of another exemplary implementation of a dispenser;

FIG. 16 illustrates by process flow chart an exemplary method of use of a dispenser; and, FIG. 17 illustrates by perspective view portions of yet another exemplary implementation of a dispenser.

Figure 3:
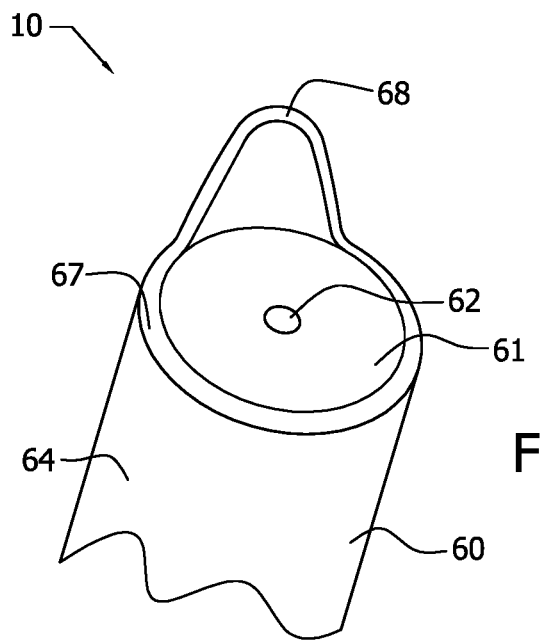
FIG. 3 illustrates by perspective view portions of the exemplary implementation of the dispenser of FIG. 1.

The Figures are exemplary only, and the implementations illustrated therein are selected to facilitate explanation. The number, position, relationship and dimensions of the elements shown in the Figures to form the various implementations described herein, as well as dimensions and dimensional proportions to conform to specific force, weight, strength, flow and similar requirements are explained herein or are understandable to a person of ordinary skill in the art upon study of this disclosure. Where used in the various Figures, the same numerals designate the same or similar elements. Furthermore, when the terms "top," "bottom," "right," "left," "forward," "rear," "first," "second," "inside," "outside," and similar terms are used, the terms should be understood in reference to the orientation of the implementations shown in the drawings and are utilized to facilitate description thereof. Use herein of relative terms such as generally, about, approximately, essentially, may be indicative of engineering, manufacturing, or scientific tolerances such as ±0.1%, ±1%, ±2.5%, ±5%, or other such tolerances, as would be recognized by those of ordinary skill in the art upon study of this disclosure.

DETAILED DESCRIPTION OF THE INVENTION

A dispenser apparatus and related methods for dispensing a unit dose of liquid by spray from a hermetically sealed container are disclosed herein. The spray emitted from the dispenser may have precise and repeatable spray characteristics.

In various aspects, the dispenser includes a piston that is slidably receivable within the container. The container contains the liquid to be sprayed in a unit dose, and a covering of rigid construction sealingly engages the container to hermetically seal the liquid within the container. A cutting edge may be disposed about a piston face of the piston to open the covering as the piston is aligned with the container, in various aspects. The dispenser includes a nozzle fluidly communicating with the piston such that the nozzle sprays liquid communicated to the nozzle by advancement of the piston within the container, in various aspects. In various aspects, the dispenser may include a container assembly that includes the container, and the dispenser may include a sleeve surrounding the piston configured to engage the container assembly. Various arms, grippable surfaces, and the like may be formed about the dispenser including the sleeve and the container assembly, and the user may manipulate the dispenser using these arms, grippable surfaces, and the like.

In operation, the user may manipulate the dispenser thereby opening the covering and then aligning the piston with the container. Opening includes, without limitation, cutting, piercing, cleaving, bursting, parting, or otherwise causing the covering to fail thereby opening the cover. The covering may be engineered to include weak points at which the covering will open upon being engaged with the piston. The covering may include concentrated stress points at which the stress induced by the piston is concentrated thereby causing the covering to open through failure of the covering material at the concentrated stress points upon engagement of the covering with the piston. The user may advance the piston so that the cutting edge first contacts the covering and then opens the covering. The cutting edge, which is disposed about the piston face of the piston, extends forth from the piston face to contact the covering and then opens the covering prior to engagement of the piston with the container, in various aspects. Following the opening of the covering by the cutting edge, the piston may be further advanced into alignment with the container. The piston may be aligned with the container as the piston is advanced in engagement with the container by shoulders formed about the circumference of the piston face of the piston, in various aspects. The piston may be advanced through the opened covering as the piston is aligned with the container. Following alignment with the container, the piston may be advanced within the container thereby expelling liquid from the container as spray from the nozzle, which is in fluid communication with the piston, and, thence, the liquid within the container, in various aspects.

Opening the covering with only the cutting edge in contact with the covering may reduce or eliminate pressure spikes in the liquid pressure as the covering is opened because only the cutting edge and not the piston contacts the covering to open the covering. The covering may be rigid to minimize deformation of the covering as the covering is being opened, which may reduce or eliminate pressure spikes in the liquid.

In various aspects, the piston is aligned with the container following opening of the covering. Following alignment with the container, the piston is advanced within the container in engagement with the liquid thus spraying a unit dose of liquid from the container. A passage formed between a piston face of the piston and the nozzle conveys the liquid from the container through the nozzle, which emits the liquid as a spray, in various aspects. By manipulation of the dispenser, the user may control the advancement rate of the piston within the container, thereby controlling the liquid pressure developed within the liquid by the piston and the flow rate at which the liquid is sprayed from the nozzle. Note that the flow rate equals the rate at which the piston displaces the volume of the container, and the liquid pressure is related to the force applied to the liquid by the piston, both of which may be controlled by the user. The spray characteristics of the spray from the nozzle may be related to the liquid pressure and the flow rate, so that the user may control the spray characteristics by controlling the advancement rate of the piston and the force applied to the liquid by the piston.

In various aspects, the dispenser is formed so that the displaced volume of liquid that is displaced when the piston is aligned with the container to be slidingly engaged with the container and engaged with the liquid to be positioned to initiate controlled dispensing of the liquid is less than the priming volume. The priming volume is the volume of the passage(s) between the piston face of the piston and the nozzle exit of the nozzle. Making the displaced volume less than or equal to the priming volume may eliminate wastage of liquid from the nozzle caused by spikes in the liquid pressure during opening of the covering and alignment of the piston with the container.

Spray characteristics of the spray from the nozzle may include the flow rate, spray angle, spray pattern, spray quality, droplet spectrum, distribution on target, and droplet drift. Spray quality may be expressed in terms of its average droplet size, and spray quality may be an indicator of droplet drift, which may be undesirable. Droplet drift characterizes the portions of the spray that does not reach an intended target due to factors such as air velocity (wind), spray height, operating speed, air temperature, and humidity.

The spray characteristics of the spray may be important in various applications, and the desired spay characteristics may vary depending upon the particular application. The spray may be formed of droplets having a find droplet size some applications, while the spray may be formed of droplets having a coarse droplet size in other applications. For example, droplet sizes less than about 150 microns may be used for applications where the coverage of the spray is to be maximized. Coarse droplet sizes of around 300 microns may be used in applications that seek to minimize spray drift, which may cause the spray to miss a target, in order to direct the maximum amount of spray onto the target. Note that droplets generally less than about 100 microns may be prone to drift, so that it may be desirable to avoid droplets less than about 100 microns.

The absence of a pressure spike in the liquid pressure coupled with control of the liquid pressure and the liquid velocity by control of the advancement of the piston within the container, in various aspects, may enhance the ability of the user to produce spray having consistent spray characteristics from the dispenser. Because the nozzle may produce different droplet sizes at different pressures, controlling the liquid pressure of the liquid within the container as the piston is inserted into the container and controlling the liquid pressure as the piston is advanced within the container may enhance control of the spray characteristics including the droplet size. The user may visually monitor the spray characteristics of the spray and adjust the advancement rate of the piston within the container to control the spray characteristics of the spray during dispensation of the unit dose. Such visual monitoring by the user may constitute a feedback mechanism, which may be inherent in the dispenser. Consistent opening of the covering from container to container may allow the user to develop facility with the dispenser thereby allowing the user to produce consistent spray characteristics.

In various aspects, the nozzle is formed as a pressure-atomizing nozzle. In various aspects, the nozzle includes a swirl chamber. Nozzles including a swirl chamber may produce sprays having better spray characteristics in comparison with the spray characteristics of spray produced by a pressure-atomizing nozzle. The dispenser may include two or more interchangeable nozzles, in various aspects selectable to produce spray having selected spray characteristics.

The nozzle, in various implementations, may be formed, for example, as a flocked tip nozzle, brushed tip nozzle, porous tip nozzle, wetted tip nozzle, or other such nozzle capable of depositing liquid upon an application surface. Spray, as used herein, includes the liquid discharges from, for example, a flocked tip nozzle, brushed tip nozzle, porous tip nozzle, or wetted tip nozzle. Spay characteristics includes characteristics of the liquid discharges from, for example, a flocked tip nozzle, brushed tip nozzle, porous tip nozzle, or wetted tip nozzle. The characteristics of such liquid discharges may include the thickness of the liquid deposited upon the application surface, the width of the liquid deposited upon the application surface, or other such characteristics, as would be readily recognized by those of ordinary skill in the art upon study of this disclosure. The tip nozzle may be wetted in a controllable and precise manner as liquid is transferred from the wetted tip to the application surface by sliding the wetted contact area over the application surface. For a uniform application of the liquid, the rate at which the liquid is dispensed should be proportional to the rate at which the contact surface slides over the application surface. The rate at which a porous or flocked contact tip nozzle is wetted is controlled by the user through the advancement of the piston and the force applied to the liquid. If a non-uniform application is desired, the flow rate of the liquid to the contact area is adjusted accordingly.

Higher aspect ratio cylindrical containers (height/diameter for the particular case of a cylindrical container) may give more accurate control of sprays with larger droplet sizes and less droplet drift. Lower aspect ratio cylindrical containers may give more accurate control of sprays with smaller droplet sizes.

In various aspects, the container is separable from other portions of the dispenser including the piston, sleeve, and nozzle. Use of a separable container may, for example, facilitate the filling of the container without interference from the other portions of the dispenser. Use of a separable container may, for example, facilitate thermal treatment of the liquid hermetically sealed within the container, or radiation treatment of the liquid hermetically sealed within the container without interference from the other portions of the dispenser.

The dispenser may dispense by spray multiple unit doses from multiple containers in succession, in various aspects. The dispenser may dispense multiple unit doses from a single container, in various aspects. In various aspects, the dispenser apparatus may be formed of materials such as, for example, polyethylene, polyethylene terephthalate, polypropylene, polyamides, glass, metal such as aluminum or stainless steel, synthetic or natural rubber, and combinations thereof. The material(s) may be selected based upon compatibility with the liquid to be dispensed. In various aspects, the dispenser apparatus and methods disclosed herein may be used in medical, automotive, aerospace, marine, or any other applications for application of a unit dose of liquid wherein the liquid is hermetically sealed until dispensing.

Turning now to the exemplary implementations illustrated in the various Figures, FIG. 1 illustrates exemplary dispenser 10. As illustrated in FIG. 1, dispenser 10 includes body 20. Stalk 40 extends forth from distal end 23 of body 20 with proximal end 41 of stalk 40 being secured about distal end 23 of body 20, as illustrated, and proximal end 51 of nozzle 50 secured to distal end 43 of stalk 40. The length of stalk 40, in various implementations, may be determined by the application. For example, to deliver a fluoride varnish, anti-inflammatory, or other medical agents in oral-hygiene applications, a long and slender stalk 40 may be desirable to enable comfortably reaching any desired location. To deliver medical agents in the aural or nasal passages, stalk 40 may be short in order to prevent too deep insertions of the dispensing device that may be harmful.

Nozzle outlet 52 is formed in distal end 53 of nozzle 50, in this implementation, and spray 14 may be sprayed forth from nozzle outlet 52 of nozzle 50. In various other implementations, the stalk 40 may have various lengths, bends, and other such configurations. One or more nozzle outlets, such as nozzle outlet 52, may be located about various portions of nozzle 50, to spray the spray 14 in various orientation(s) with respect to nozzle 50. Some implementations may omit stalk 40 entirely. In such implementations, the nozzle, such as nozzle 50, may be located within body 20 or, for example, about distal end 23 of body 20. Nozzle 50 may be configured as a flocked tip nozzle, brushed tip nozzle, or pressure atomizing nozzle, in various implementations. Nozzle 50 may be removably secured to stalk 40 so that nozzle 50 may be interchangeably selectable from a plurality of differing nozzles, such as, for example, a brushed tip nozzle or a flocked tip nozzle.

Body 20 includes arms 27, 29 that extend forth from outer surface 32 of body 20, as illustrated in FIG. 1. Arms 27, 29 include grippable surfaces 28 that may be formed, for example, as checkering, corrugations, indentations, roughening, patterning, or combinations thereof on portions of the surface of arms 27, 29. Grippable surface 28 in conjunction with arms 27, 29 may enhance the gripping of arms 27, 29 by the user to facilitate the user's manipulation of dispenser 10. Other implementations may include a single arm, such as arm 27 or arm 29, that extends circumferentially around body 20. Still other implementations, may include additional arms, such as arms 27, 29, and the arms may assume various shapes, for example, with holes or curves that accommodate the finger(s) or hand(s) of the user. Grippable surfaces, such as grippable surface 28, may be variously formed about the arm(s) or body 20, in various implementations. A grippable surface, such as grippable surface 28, may be formed about proximal end 71 of container assembly 70 to allow the user to apprehend proximal end 71 with the thumb, in various implementations.

Dispenser 10 includes container assembly 70 that is insertably received within body 20 through proximal end 21 of body 20, as illustrated in FIG. 1. Key 74, which is formed as a protuberance on outer surface 72 of container assembly 70, engages male-female with keyway 24, which is formed as a slot in body 20, in this implementation. The slidable interlocking engagement between key 74 and keyway 24 illustrated in FIG. 1 may orient the container assembly 70 with respect to body 20 and may prevent rotation of container assembly 70 as container assembly 70 is advanced into body 20 through proximal end 21 in implementations wherein container assembly has a cylindrical shape with a cylindrical cross-section. Key 74 and keyway 24 may be formed with various combinations of male elements—e.g. flanges, rails, protuberances—and corresponding female elements—e.g. slots, grooves, channels—to allow key 74 of container assembly 70 to slidably engage keyway 24 of body 20, in various other implementations. The male element(s), such as key 74, and the corresponding female element(s), such as keyway 24, may be variously distributed between body 20 and container assembly 70, in various other implementations. Some implementations may omit key 74 and keyway 74.

In various implementations, key 74 and keyway 24 may be formed as a safety lock. For example, container assembly 70 may be inserted within body 20 as distributed from a supplier but may be unable to engage piston until key 74 and keyway 24 are engaged with one another, thereby preventing inadvertent premature opening of container 80 of container assembly 70. Key 74 and keyway 24 may be engaged with one another by rotation of container assembly 70 within sleeve 30, in various implementations.

As illustrated in FIG. 2, body 20 forms both sleeve 30 and piston 60, and sleeve 30 and piston 60 are of generally a unitary piece. Inner surface 34 of sleeve 30 defines chamber 36. Piston 60 extends forth from body 20 into chamber 36 proximate distal end 23 of body 20, and piston face 61 of piston 60 is oriented toward proximal end 21 of body 20, as illustrated. Inlet 62 is formed in piston face 61 of piston 60, and inlet 62 communicates with passage 65, which is formed within piston 60. Passage 65, in turn, communicates with passage 45 within stalk 40, passage 45 communicates with passage 55 within nozzle 50, passage 55 communicates with passage 57 within nozzle 50, and passage 57 communicates with nozzle outlet 52. Accordingly, liquid 12 may pass into inlet 62 into passage 65, through passages 65, 45, 55, 57, respectively, and from passage 57 through nozzle outlet 52, in this implementation. Passage 57 has a smaller cross-section than passage 55, in this implementation, so that the liquid 12 is accelerated as the liquid 12 passes from passage 55 through passage 57 to exit nozzle 50 through nozzle outlet 52 as spray 14. In certain implementations, for example, implementations wherein nozzle 50 is formed as a porous tip or flocked tip, passage 57 may have a larger cross section than passage 55 to allow the liquid to wet nozzle 50 uniformly through capillary and convective fluid motion.

Container assembly 70 is insertably received within chamber 36 of sleeve 30 through proximal end 21 of body 20, as illustrated in FIG. 2., with distal end 73 of container 70 oriented toward piston face 61 of piston 60. Key 74 is slidably engaged with keyway 24, as illustrated, and key 74 may be so engaged with keyway 24 as container assembly 70 is inserted into chamber 36. In other implementations, container assembly 70 may be rotated within sleeve 30 to engage keyway 24 with key 74.

Container 80 is formed within portions of container assembly 70, in the implementation of FIG. 2, and reservoir 86 of container 80 is defined by surface 75 of container assembly 70, inner surface 82 of container assembly 70, and inner surface 91 of covering 90. Accordingly, in this implementation, apart from covering 90, container 80 and container assembly 70 are formed a unitary structure. The container assembly, such as container assembly 70, and the container, such as container 80, may be separable elements that may be, for example, slidably engaged with one another to allow replacement of the container within the container assembly, in other implementations (see FIG. 12).

Covering 90 is sealingly engaged about distal end 73 of container assembly 70 by hermetic seal 94 to enclose sealingly reservoir 86 of container 80 and liquid 12 therein, in this illustrated implementation. Covering 90 may be formed of, for example, metal foil, various plastics, glass, or other such materials, as would be readily recognized by those of ordinary skill in the art upon study of this disclosure. The foil, for example, may be aluminum covered in part with a liquid-compatible coating, so that surface 91 of covering 90 is compatible with liquid 12.

Piston 60 is formed to be insertable through covering 90 into reservoir 86 of container 80 to be aligned with container 80 in the implementation of FIG. 2. When so aligned, piston face 61 is faced toward surface 75 and piston side 64 is faced toward surface 82. Piston side 64 may be sealingly slidably biased against surface 82 to prevent leakage of liquid 12 between piston side 64 and surface 82 as piston 60 is advanced within reservoir 86 toward surface 75. Annular slot 37, which is generally defined by inner surface 34 of sleeve 30 and piston side 64 of piston 60, is sized to accommodate wall 77 of container assembly 70 as piston 60 is advanced within reservoir 86, and annular slot 37 extends sufficiently toward distal end 23 to allow piston 60 to advance within reservoir 86 until piston face 61 contacts surface 75, which is the limit of advance of piston 60, in this implementation.

FIG. 3 further illustrates piston 60 of dispenser 10. As illustrated in FIG. 3, inlet 62 is located at the center of circularly shaped piston face 61. Shoulder 67 is formed about the periphery of piston face 61 of piston 60, and portions of shoulder 67 extend forth from piston face 61 and are tapered into a point to form cutting edge 68, as illustrated.

Figure 4:
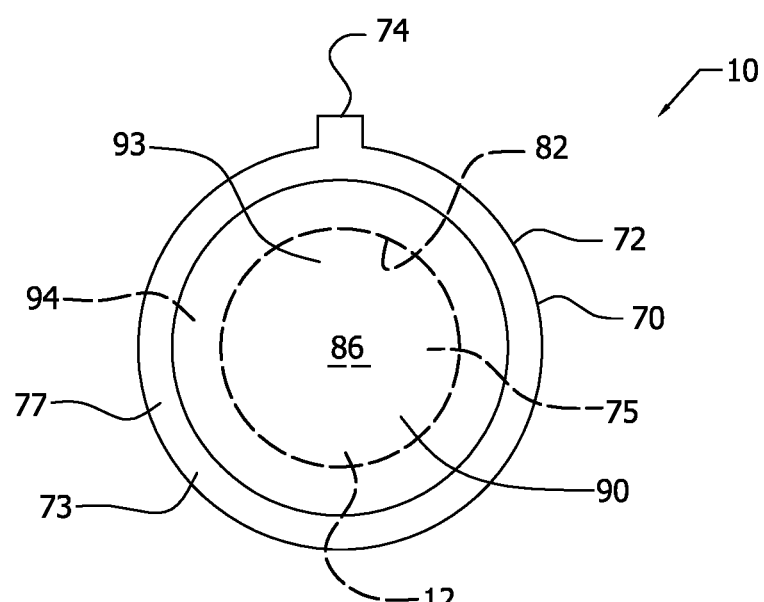
FIG. 4 illustrates by frontal view portions of the exemplary implementation of the dispenser of FIG. 1.

FIG. 4 further illustrates container assembly 70 and container 80. As illustrated in FIG. 4, key 74, which is rectangular in shape, extends forth from outer surface 72 of container assembly 70 to engage keyway 24 in body 20. Keyway 24 is formed as a rectangular slot configured to receive rectangular key 74 therein, in this implementation. Covering 90 covers reservoir 86 extending to overlap portions of wall 77, as illustrated. Covering 90 is bonded to portions of wall 77 at distal end 73 that faces piston surface 61 of piston 60 to form hermetic seal 94, in this implementation. Hermetic seal 94 extends around the entire circumference of wall 77, which is circular in shape, to hermetically seal liquid 12 within reservoir 86, in this implementation. In other implementations such as that in FIG. 6, covering 290 may be bonded to inner surface 282 of container 280 to form hermetic seal 294. In the implementation of FIG. 4, inner surface 82 of container 80 is circular in shape in conformance to the circular shape of piston side 64 of piston 60 (see FIG. 3), so that piston side 64 may be sealingly slidably biased against surface 82 as piston 60 is advanced within reservoir 86 toward surface 75.

In operation, the user may insert container assembly 70 into chamber 36 of sleeve 30. Container assembly 70 includes container 80 with liquid 12 hermetically sealed within reservoir 86 by covering 90, in this implementation. As the user inserts container assembly 70 into sleeve 30, in this implementation, key 74 of container assembly 70 is engaged with keyway 24 of sleeve 30, which orients container assembly 70 with respect to sleeve 30 and piston 60, and prevents rotation of container assembly 70 within sleeve, particularly as piston 60 engages container assembly 70 including container 80.

With the container assembly 70 inserted into sleeve 30, the user may, for example, grasp body 20 by arms 27, 29 using the index finger and the middle finger, and the user may press upon proximal end 71 of container assembly 70 with the thumb to force piston 60 through covering 90 into reservoir 86 to be aligned with container 80. With piston 60 aligned with container 80, the user may press upon arms 27, 29 and proximal end 71 to advance piston 60 within reservoir 86 until piston face 61 contacts surface 75 thereby administering a unit dose of liquid 12 as spray 14 from dispenser 10.

FIGS. 5A-5E illustrate operational stages 103, 107, 109, 115, 119 respectively, of dispenser 10 as piston 60 is forced through covering 90, piston 60 is aligned with reservoir 86 of container 80, and then piston 60 is advanced within reservoir 86 to dispense a unit dose of liquid 12 from container 80 as spray 14. With container assembly 70 received within sleeve 30, the user may press upon arms 27, 29 and proximal end 71 to slidably advance piston 60 and container assembly 70 toward one another thereby progressing consecutively through exemplary operational stages 103, 107, 109, 115, 119.

Figure 5A:
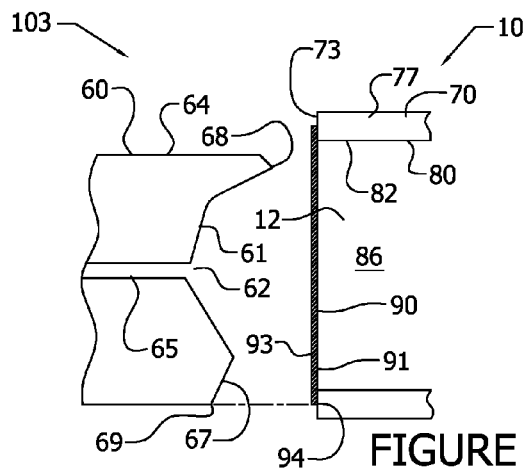
FIG. 5A illustrates by side view portions of the exemplary implementation of the dispenser of FIG. 1 at a first operational stage.

FIG. 5A illustrates piston 60 and container assembly 70 at operational stage 103 wherein piston 60, including cutting edge 68 on piston face 61 of piston 60, is set apart from container assembly 70 including container 80 and covering 90. Piston 60 may be proximate container assembly 70 and piston 60 and container assembly 70 may be advancing toward one another as manipulated by the user, at operational stage 103.

As illustrated in FIG. 5A, piston face 61 has a concave shape between shoulder 67 and inlet 62 curving inward from shoulder 67 toward inlet 62. In other implementations, piston face 61 may be flat thereby forming a right angle with respect to piston side 64. As illustrated in FIG. 5A, piston 60 includes shoulder 67 that extends around piston face 61 at the periphery of piston face 61. In this implementation, portions of shoulder 67 are formed as an angled surface. Portions of shoulder 67 extend forth to form cutting edge 68, as illustrated. As indicated by the dash-dot line in FIG. 5A, piston 60 and container assembly 70 are misaligned with one another at operational stage 103, so that distal end 73 of container assembly 70 will strike shoulder 67 of piston 60 as piston 60 and container assembly 70 are advanced toward one another. Shoulder 67 functions to correct such misalignment, when necessary, by aligning piston 60 with container 80 thereby allowing piston 60 to be inserted into reservoir 86 of container 80. Some implementations may omit the shoulder, such as shoulder 67.

Figure 5B:
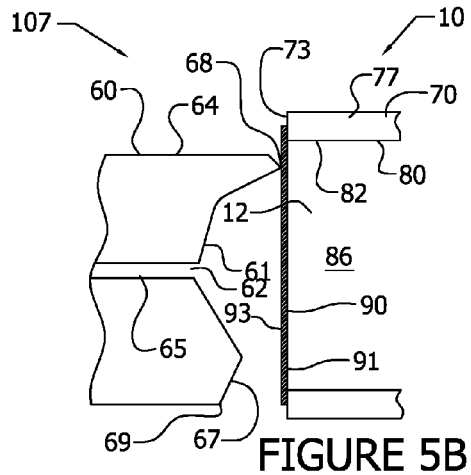
FIG. 5B illustrates by side view portions of the exemplary implementation of the dispenser of FIG. 1 at a second operational stage.

FIG. 5B illustrates operational stage 107 of dispenser 10. At operation stage 107, cutting edge 68 contacts outer surface 93 of covering 90, as illustrated. The portions of shoulder 67, other than those portions of shoulder 67 that form cutting edge 68, are set apart from container assembly 70 including wall 77, which forms a portion of container 80, in this implementation. Covering 90 is sufficiently rigid so that covering 90 does not bend appreciably into reservoir 86, which would create liquid pressure in liquid 12, as cutting edge 68 opens covering 90. The protrusion of cutting edge 68 from piston face 61 is exaggerated for illustrative purposes in the Figures. Cutting edge 68 may protrude in the range of 10% of the hydraulic diameter (see equation 1) of piston 60, in various implementations.

While the process of opening covering 90 may be cutting-tip dependent, covering dependent, and dependent on how much gas is present next to the liquid in the container, dispenser 10 opens the covering before any appreciable liquid pressurization takes place. This is likely the case with most applications where a gas is present in the container with the liquid and where the uncompressed volume of gas is substantially less than the volumetric displacement caused by the deformation of the covering by the cutting surface prior to the actual opening of the covering, which would relieve the pressure.

Figure 5C:
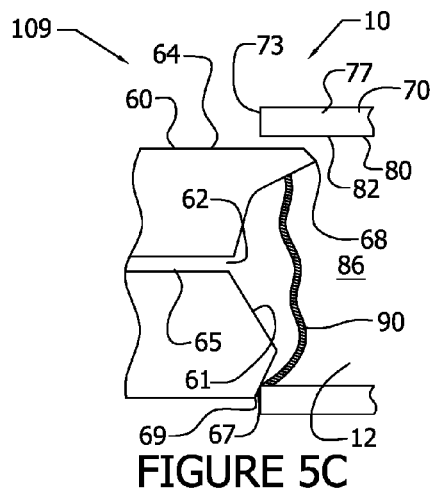
FIG. 5C illustrates by side view portions of the exemplary implementation of the dispenser of FIG. 1 at a third operational stage.

FIG. 5C illustrates operational stage 109 of dispenser 10. At operation stage 109, cutting edge 68 penetrates covering 90 from outer surface 93 through inner surface 91 to open covering 90, as illustrated. Only cutting edge 68 contacts covering 90 as covering 90 is opened during the progression from operational stage 107 to operational stage 109. The opened covering 90 is included in FIG. 5C, but is omitted from FIGS. 5D, 5E for clarity.

At operational stage 109, distal end 73 of container assembly 70 contacts shoulder 67 of piston 60 following opening of covering 90 by cutting edge 68, as illustrated, due to misalignment between piston 60 and container assembly 70. The misalignment shown in the Figures may be exaggerated for illustrative purposes. Misalignment may be less than 1% of the hydraulic diameter (see equation 1) of piston 60, in various implementations. The contact between distal end 73 and shoulder 67 may seal reservoir 86, at least in part, thereby preventing escape of liquid 12 from reservoir 86 following opening of covering 90 as piston 60 is inserted into reservoir 86. The progression from operational stage 109 to operational stage 115 (see FIG. 5D) exemplifies the alignment of piston 60 into reservoir 86. Recognizing that distal end 73 is circumferential, other portions of distal end 73 not included in the illustration may be otherwise misaligned with piston 60. Alternatively, piston 60 may be aligned with container assembly 70, in which case piston side 64 sealingly engages portions of inner surface 82 proximate distal end 73 thereby retaining liquid 12 within reservoir 86 upon opening covering 90.

Figure 5D:
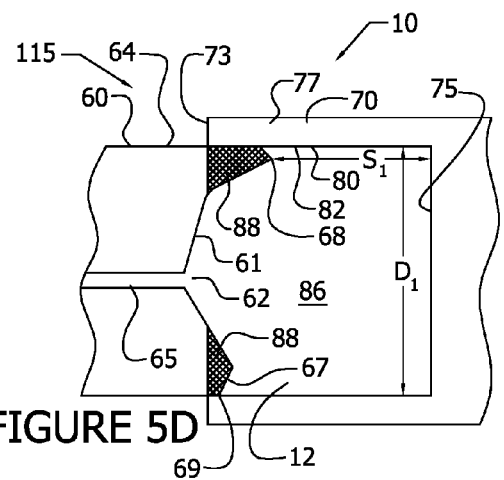
FIG. 5D illustrates by side view portions of the exemplary implementation of the dispenser of FIG. 1 at a fourth operational stage.

FIG. 5D illustrates operational stage 115 of piston 60 with respect to container assembly 70 including container 80 with covering 90. Between operational stage 109 and operational stage 115, distal end 73 of container assembly 70 slides over shoulder 67 thereby aligning piston 60 with reservoir 86 of container 80, if necessary, thus enabling the advancement of piston 60 into reservoir 86 of container 80 between operational stages 115 and 119.

At operational stage 115, piston 60 is aligned with reservoir 86 of container 80, as illustrated in FIG. 5D. Edge 69 formed between piston face 61 and piston side 64 is positioned slightly past distal end 73 within reservoir 86 of container 80 so that portions of piston side 64 of piston 60 are slidingly sealingly biased circumferentially against inner surface 82 of container 82 at exemplary operational stage 115. The sealing biasing of piston side 64 of piston 60 against inner surface 82 of container 80 prevents leakage of liquid 12 between piston side 64 and inner surface 82 at exemplary operational stage 115. The sliding sealing biasing of piston side 64 against inner surface 82 prevents leakage of liquid 12 between piston side 64 and inner surface 82 as piston 60 is advanced within reservoir 86 during the progression from operational stage 115 to operational stage 119 (see FIG. 5E).

The process of aligning piston 60 with reservoir 86 of container 80 encompasses the progression from operational stage 109, illustrated in FIG. 5C, to operational stage 115, illustrated in FIG. 5D, in this implementation. Piston 60 including the curvature, if any, of piston face 61 and the cutting edge 68 that extends forth from piston face 61 may be sized so that the displaced volume 88 with piston 60 aligned with reservoir 86 at operational stage 115 (illustrated by the cross-hatched region in FIG. 5D) is less than priming volume 59, which is the volume of passages 65, 45, 55, 57 between inlet 62 in piston face 61 of piston 60 and nozzle outlet 52 in order to avoid wastage of liquid from nozzle 50 caused by displacement of liquid 12 during inserting piston 60 into reservoir 86 of container 80. Piston 60, passages 65, 45, 55, 57, or both may be sized or otherwise formed accordingly. Displaced volume 88 is the volume of liquid 12 displaced by piston 60 as piston 60 is inserted into container 80 and equals the volume of those portions of piston 60 that lie within container 80 at operational stage 115, in this implementation.

Figure 5E:
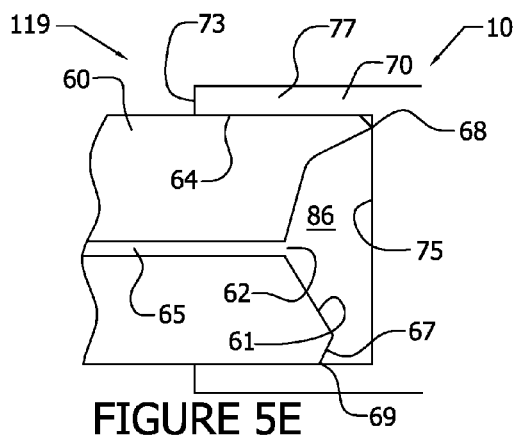
FIG. 5E illustrates by side view portions of the exemplary implementation of the dispenser of FIG. 1 at a fifth operational stage.
Figure 5F:
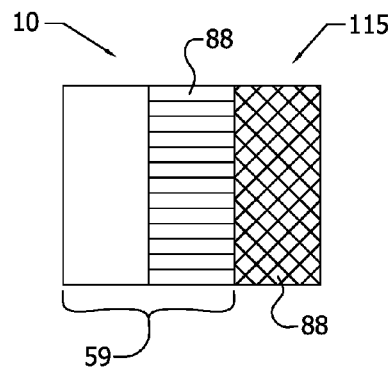
FIG. 5F illustrates schematically volumetric relationships within the exemplary implementation of the dispenser of FIG. 1 at the fourth operational stage as illustrated in FIG. 5D.

FIG. 5F presents this schematically with the displaced volume 88 illustrated as the crosshatched region. Priming volume 59, as illustrated schematically in FIG. 5F, equals the volume of passages 65, 45, 55, 57 between inlet 62 in piston face 61 of piston 60 and nozzle outlet 52 in this implementation. Following alignment of piston 60 with reservoir 86 at operational stage 115, the displaced volume 88 occupies a portion of priming volume 59 as indicated by the striped region in FIG. 5F. Displaced volume 88 may occupy all of priming volume 59 or essentially all of priming volume 59, in various implementations.

Operational stage 119 is illustrated in FIG. 5E. At operational stage 119, as illustrated, piston 60 has been advanced within reservoir 86 of container 80 such that at least portions of piston face 61 of piston 60 are biased against surface 75 of container 80.

As piston 60 is advanced within container 80 during the progression from operational stage 115 to operational stage 119 to deliver a unit dose of liquid 12 from container 80, liquid 12 is forced from reservoir 86 through inlet 62 into passage 65, through passages 65, 45, 55, 57, in progression, and from passage 57 through nozzle outlet 52. Liquid 12 is sprayed forth as spray 14 from nozzle outlet 52 of nozzle 50 during delivery of the unit dose of liquid 12.

The user may direct the spray 14 toward a target by orienting nozzle outlet 52 toward the target. The user may regulate the spray characteristics of the spray 14 emitted from dispenser 10, for example, by controlling the force applied by the forefinger, the middle finger, and the thumb to arms 27, 29 of body 20 and proximal end 71 of container assembly 70. The user may observe the spray characteristics of the spray 14 emitted from dispenser 10, and the user may adjust the force applied to arms 27, 29 and proximal end 71 of container assembly 70 to adjust the spray characteristics in order to obtain the desired spray characteristics.

As the unit dose of liquid 12 is delivered from container 80, the piston 60 moves with piston stroke $S_1$, illustrated in FIG. 5D, as piston 60 is advanced within container 80 from alignment with container 80 at operational stage 115 to biasing of at least portions of piston face 61 against surface 75 of container 80 at operational stage 119. Container 80 is cylindrical with circular cross-section of diameter D and hydraulic diameter $D_H$ given by $$D_H = \frac{4 \text{ area}}{\text{perimeter}} \quad (1)$$

where area in equation (1) is the cross-sectional area of the cross-section and the perimeter is the perimeter of the cross-section. For a circular cross-section of diameter D, then $D_H=D$. The hydraulic diameter $D_H$ may be defined for non-circular cross sections using equation (1). For example, for a square cross section of side B, then $D_H=B$.

In implementations wherein the piston stroke $S_1$ is larger than the hydraulic diameter $D_H$ of the container may produce an even and controlled low flow of spray 14 from dispenser 10. In implementations wherein the piston stroke $S_1$ is less than or equal to the hydraulic diameter $D_H$ of the container may produce an even and controlled high flow of spray 14 from dispenser 10. An aspect ratio $A_R$ may be defined as $$A_{R1}=S_1/D_H \quad (2)$$

In implementations with $A_{R1} \geq 2$ (a slender container), the flow rate and liquid pressure is smaller during advancement of the piston from operational stage 115 to operational stage 119, that may produce larger, less drift-prone droplets in spray 14.

In implementations with $A_{R1}\leq 1$, the flow rate and liquid pressure is larger during advancement of the piston from operational stage 115 to operational stage 119, causing smaller droplets in spray 14 that may result in wider spray coverage and a more delicate control of the thickness of liquid layers delivered to a surface. This decrease in average droplet size in spray 14 increases the specific surface area thereby enhancing the vaporization of the liquid, which might be desirable in certain applications.

The aspect ratio $A_{R1}$ of the container may be dictated by the desired liquid-delivery characteristics. Whereas in applications, for example, where medical inhalants are required to be vaporized, a short piston stroke with a low aspect ratio container 80 may be appropriate. When applying a numbing agent or a medical adhesive to the skin in the open air, a longer piston stroke with a higher-aspect ratio container 80 may be more appropriate to prevent droplet drift.

Another exemplary implementation of a dispenser 200 is illustrated in FIG. 6. As illustrated in FIG. 6, piston 260 and sleeve 230 of dispenser 200 are generally formed as a unitary piece as portions of body 220. Chamber 236 is defined by inner surface 234 of sleeve 230, and piston 260 extends forth from body 220 into chamber 236 such that piston face 261 of piston 260 is oriented toward proximal end 221 of body 220, as illustrated.

Container assembly 270 is insertably received within chamber 236 of sleeve 230 through proximal end 221, as illustrated in FIG. 6, with distal end 273 of container 270 oriented toward piston face 261 of piston 260. Key 274 is slidably engaged with keyway 224 to allow container assembly 270 to slide within chamber 236, as illustrated.

As illustrated in FIG. 6, container 280 is formed within portions of container assembly 270, and reservoir 286 of container 280 is defined by surface 275 of container assembly 270, inner surface 282 of container assembly 270, and inner surface 291 of covering 290. Accordingly, in this implementation, container 280, apart from covering 290, is formed as a unitary structure with container assembly 270. Covering 290 is sealingly engaged about inner surface 282 proximate distal end 273 of container assembly 270 by hermetic seal 294 to enclose sealingly reservoir 286 of container 280 and liquid 212 therein, in this illustrated implementation.

Piston 260 may be forced through covering 290 and then aligned with reservoir 286 of container 280, in the implementation of FIG. 6. When so aligned, piston face 261 is faced toward surface 275 and piston side 264 is faced toward inner surface 282. Portions of piston side 264 proximate piston face 261 engage inner surface 282 proximate end 273 when piston 260 is aligned with reservoir 286 of container 280. Piston side 264 may be sealingly slidably biased against inner surface 282 to prevent leakage of fluid 212 between piston side 264 and inner surface 282 when piston 260 is aligned with reservoir 286 and as piston 260 is advanced within reservoir 286 toward surface 275. Annular slot 237, which is generally defined by inner surface 234 of sleeve 230 and piston side 264 of piston 260, is sized to accommodate wall 277 of container assembly 270 as piston 260 is advanced within reservoir 286 toward surface 275, and annular slot 237 is sized to allow piston 260 to advance within reservoir 286 until piston face 261 contacts surface 275, in this implementation.

As illustrated in FIG. 6, inset 240 is disposed within body 220. Inset 240 is generally frustoconical in shape, in this implementation. Inset 240 may be formed separately from body 220 and then joined to inner surfaces of body 220 to form the illustrated structure. End 241 of inset 240, which forms the frustum, protrudes forth from piston face 261 of piston 260, with end 241 formed into cutting edge 268 for the opening of covering 290, in this implementation. Recess 279 in surface 275 is configured to receive therein the portion of inset 240 that protrudes forth from piston face 261 so that piston face 261 may be biased against surface 275.

Slots 333, 343 are formed in surface 242 and in end 243 of inset 240 to define passages 335, 345, respectively, when surface 242 of inset 240 is joined to inner surface 226 of body 220, as illustrated in FIG. 6 (see also FIGS. 7B, 7D). Passages 335, 345 fluidly communicate with swirl chamber 256 of nozzle 250, as illustrated. Nozzle 250 is configured as a pressure atomizing nozzle, in this implementation. As illustrated in FIG. 6, liquid 212 may pass through inlets 321, 329 into passages 335, 345, respectively, then from passages 335, 345 into swirl chamber 256, and exit swirl chamber 256 through convergent passage 257 (see FIG. 7C) and thence through nozzle outlet 252 as spray, such as spray 14.

FIG. 7A illustrates end 241 of inset 240 that protrudes forth from piston face 261 of piston 260. As illustrated in FIG. 7A, end 241 includes recess 247 with cutting edge 268 formed radially about the centerline of inset 240. Cutting edge 268 may be set at various radial distances from the centerline, in various implementations, and inset 240 may be sized accordingly. Cutting edge 268 extends forth from piston face 261 of piston 260, as illustrated, or may be slanted to minimize further the initial contact are with membrane 290, increasing the piercing pressure and thus decreasing any deformation of membrane 290 prior to opening of membrane 290.

FIG. 7B illustrates inset 240 received by body 220 at piston face 261 of piston 260. As illustrated in FIG. 7B, cutting edge 268 is disposed circularly about recess 247. Surface 242 of inset 240 is joined to inner surface 226 of body 220 to secure inset 240 to body 220. Inlets 321, 323, 327, 329 are disposed about end 241 of inset 240, and liquid may pass through inlets 321, 323, 327, 329 into passages 335, 347, 345, 349, respectively (see also FIG. 7D). Passages 347, 349 may defined by slots, such as slots 333, 343 (see FIG. 6) formed in surface 242 and in end 243 of inset 240 when surface 242 of inset 240 is joined to inner surface 226 of body 220. The inner surface 226 of body 220 in conjunction with the slots in surface 242 of inset 240 defines passages 335, 347, 345, 349, in this implementation. Portions of surface 242 between the slots are joined to inner surface 226, in this implementation, and these portions of surface 242 may be bonded to inner surface 226. Various other implementations may include various numbers of inlets, such as inlets 321, 323, 327, 329, and the inlets may be variously disposed about end 241 of inset 240. Because of the frustoconical shape of inset 240, passages 335, 347, 345, 349 have a conical arrangement with respect to one another, in this implementation.

FIG. 7C illustrates portions of dispenser 200 proximate distal end 223 of body 220, including swirl chamber 256 and nozzle outlet 252. As illustrated in FIG. 7C, passages 335, 345, pass along side 242 of inset 240 and end 243 of inset 240 to communicate fluidly into swirl chamber 256. Swirl chamber 256 is a generally cylindrical shaped region that transitions into convergent passage 257 and thence into outlet 252, as illustrated. The cross-sectional area of convergent passage 257 converges from swirl chamber 256 to outlet 252.

FIG. 7D illustrates passages 335, 347, 345, 349 in communication with swirl chamber 256. Passages 335, 347, 345, 349 connect tangentially to swirl chamber 256 to induce swirl into liquid 212 as liquid 212 flows from passages 335, 347, 345, 349 into swirl chamber 256. This swirl in liquid 212 is increased by conservation of angular momentum as liquid 212 is accelerated by passage through convergent passage 257 from swirl chamber 256 to outlet 252. A spray will be formed as the swirling liquid 212 is released through outlet 252. In various implementations, the cylindrically shaped swirling chamber 256 has a bit more volume (re. height) in proportion to the volume of the convergent channel 257.

In operation of dispenser 200, the user may insert container assembly 270 into chamber 236 of sleeve 230. Container assembly 270 includes container 280 with liquid 212 hermetically sealed within reservoir 286 by covering 290. As the user inserts container assembly 270 into sleeve 230, key 274 of container assembly 270 is engaged with keyway 224 of sleeve 230, which orients container assembly 270 with respect to sleeve 230 and prevents rotation of container assembly 270 within sleeve, particularly as piston 260 engages container assembly 270.

With the container assembly 270 inserted into sleeve 230, the user may apply force to proximal end 271 of container assembly 270, for example, by pressing upon proximal end 271 with the thumb to slide container assembly 270 and sleeve 230 with respect to one another thereby inserting piston 260 through covering 290 into reservoir 286 of container 280 and then advancing piston 260 within reservoir 286 of container 280 to dispense the unit dose of liquid 212 from container 280 as spray, such as spray 14, through nozzle 250.

Figure 8A:
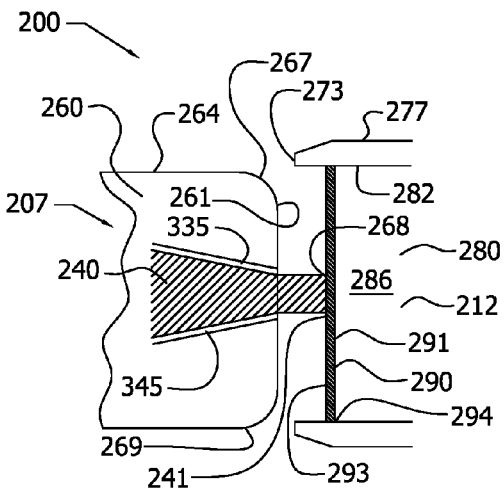
FIG. 8A illustrates by side view portions of the exemplary implementation of the dispenser of FIG. 6 at a first operational stage.

FIGS. 8A, 8B, 8C and 8D illustrate operational stages 207, 213, 215, 217, respectively, of dispenser 200. As illustrated in FIG. 8A, piston face 261 is flat between shoulder 267 and inset 240 forming a right angle with respect to piston side 264. Piston 260 includes shoulder 267 that extends circumferentially around piston face 261 at the periphery of piston face 261 proximate piston side 264, in this implementations. Shoulder 267 is curved, as illustrated, and shoulder 267 functions to correct misalignment between piston 260 and container 280 thereby aligning piston 260 with reservoir 286 of container 280. In this implementation, hermetic seal 294 is formed between covering 290 and inner surface 282 of container 280 to enclose reservoir 286 that contains liquid 212 therein.

At operation stage 207, as depicted in FIG. 8A, cutting edge 268 contacts outer surface 293 of covering 290. In this implementation, other than cutting edge 268 contacting outer surface 293, piston 260 and container assembly 270 are set apart from one another at operational stage 207. Covering 290 is sufficiently rigid so that covering 290 generally does not deform significantly into reservoir 286, which would create liquid pressure in liquid 212, as cutting edge 268 opens covering 290. This effect of deformation of the covering on liquid pressure is further minimized for containers that are not completely filled and have some gas sealed inside.

Figure 8B:
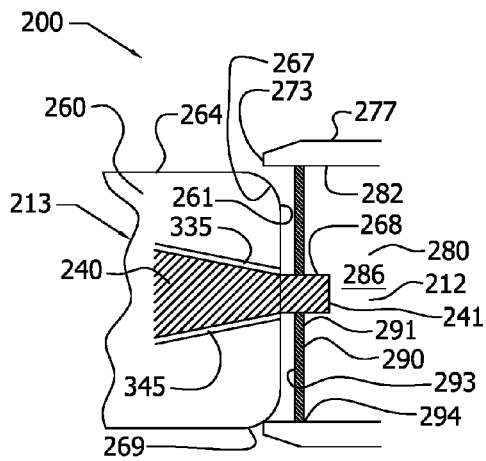
FIG. 8B illustrates by side view portions of the exemplary implementation of the dispenser of FIG. 6 at a second operational stage.

Operational stage 213 is illustrated in FIG. 8B. Piston 260 is advanced toward surface 275 of container 280 during the progression from operational stage 207 to operational stage 213, in this implementation, to open covering 290 with cutting edge 268 at end 241 of inset 240. At operation stage 213, cutting edge 268 has penetrated covering 290 from outer surface 293 through inner surface 291 to open covering 290, as illustrated. Only cutting edge 268 contacts covering 290 as covering 290 is opened during the progression from operational stage 207 to operational stage 213. Because cutting edge 268 has a circular configuration (see FIG. 7B), covering 290 is opened circumferentially in correspondence to cutting edge 268, in this implementation. Cutting edge 268 can also be slanted to increase the opening pressure upon initial contact of cutting edge 268 on covering 290, further minimizing the impact of the deformation of covering 290 into reservoir 286. Distal end 273 of wall 277 of container assembly 270 is biased against shoulder 267 of piston 260 to seal reservoir 286 thereby preventing escape of liquid 212 from reservoir 286 at operational stage 213 following the opening of covering 290.

Figure 8C:
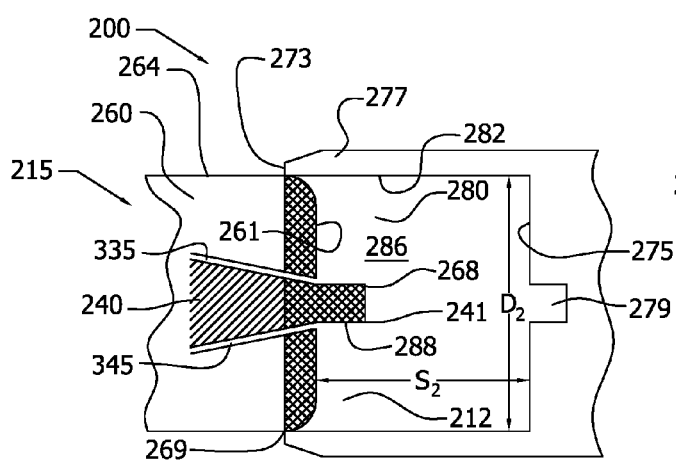
FIG. 8C illustrates by side view portions of the exemplary implementation of the dispenser of FIG. 6 at a third operational stage.

FIG. 8C illustrates operational stage 215 of dispenser 200. At operational stage 215, piston 260 is aligned with reservoir 286 of container 280. Shoulder 267 lies generally within reservoir 286 of container 80 so that portions of piston side 264 proximate piston face 261 are slidingly sealingly biased circumferentially against inner surface 282 of container 280 proximate distal end 273, as illustrated in FIG. 8C. Liquid 212 is sealed within reservoir 286 by the sealing engagement between piston side 264 and inner surface 282.

The process of aligning piston 260 with reservoir 286 of container 280 encompasses the progression from operational stage 213, illustrated in FIG. 8B, to operational stage 215, illustrated in FIG. 8C, in this implementation. Piston 260 including the curvature, if any, of piston face 261 and the portion of inset 240 that extends forth into reservoir 286 from piston face 261 may be sized so that the displaced volume 288 (illustrated by the cross-hatched region in FIG. 8C) is less than the priming volume 259. Displaced volume 288 is the volume of liquid 212 displaced by piston 260 upon alignment of piston 260 with container 280 and equals the volume of those portions of piston 260 that lie within container 280 at operational stage 215, in this implementation. The priming volume 259 may be defined as the volume of the various passages, swirl chambers, reservoirs, and so forth between piston face 261 and nozzle outlet 252 that may be filled with liquid 212 prior to the emission of liquid 212 from dispenser 200. For example, in this implementation, priming volume 259 equals the volume of passages 335, 347, 345, 349 and swirl chamber 256 between inlet 262 in piston face 261 of piston 260 and nozzle outlet 252.

Configuring the displaced volume 288 to be less than the priming volume 259 may avoid wastage of liquid from nozzle 250 caused by displacement of liquid 212 during the aligning of piston 260 with reservoir 286 of container 80. Wastage may include splashing, spraying, or other inadvertent or undesired discharge prior to application of the unit dose. Piston 260, passages 335, 347, 345, 349, or swirl chamber 256 may be sized or otherwise formed accordingly so that the displaced volume 288 is less than priming volume 259. It may be desirable to size passages 335, 347, 345, 349, and swirl chamber 256 and piston 260 such that the displaced volume 288 almost fills passages 335, 347, 345, 349, and swirl chamber 256 with liquid 212 to prime dispenser 212. Once primed, further advancement of piston 260 within reservoir 286 causes liquid 212 to be emitted as spray, such as spray 14, from nozzle 250.

Figure 8D:
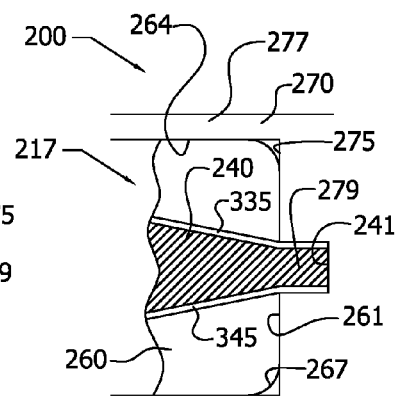
FIG. 8D illustrates by side view portions of the exemplary implementation of the dispenser of FIG. 6 at a fourth operational stage.
Figure 8E:
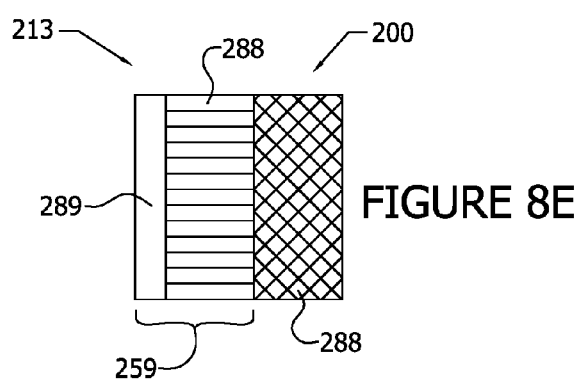
FIG. 8E illustrates schematically volumetric relationships within the exemplary implementation of the dispenser of FIG. 6 at the third operational stage as illustrated in FIG. 8C.

FIG. 8E presents this schematically with the displaced volume 288 illustrated as the crosshatched region. Priming volume 259, as illustrated schematically in FIG. 8F, equals the volume of passages 335, 347, 345, 349 and swirl chamber 256 between inlet 262 in piston face 261 of piston 260 and nozzle outlet 252, in this implementation. Following alignment of piston 260 with reservoir 286 at operational stage 215, the displaced volume 288 occupies almost all of priming volume 259 as indicated by the striped region in FIG. 8F. The displaced volume 288 will be decreased for a concave piston face that is convergent to the inlet of passages 335, 347, 345, 349 in comparison to the flat piston face 261 of this exemplary implementation.

Operational stage 217 of dispenser 200 is illustrated in FIG. 8D. At operational stage 217, as illustrated, piston 260 has been advanced within reservoir 286 from operational stage 215 to deliver the unit dose of liquid 212 as spray, such as spray 14, from nozzle 250 such that piston face 261 of piston 260 is biased against surface 275. The portion of inset 240 that extends forth from piston face 261 is received within recess 279, which allows piston face 261 to be biased against surface 275, in this exemplary implementation.

As piston 260 is advanced within container 280 in the progression from operational stage 215 to operational stage 217, liquid 212 is forced from reservoir 286 through inlets 321, 323, 327, 329 into passages 335, 347, 349, 345, respectively, through passages 335, 347, 349, 345 into swirl chamber 256, and then liquid 212 is sprayed from swirl chamber 256 of nozzle 250 though nozzle outlet 252. Dispenser 200 delivers the unit dose of liquid 212 during the progression from operational stage 215 to operational stage 217. The user may manipulate dispenser 200 including the force applied to proximal end 271 to adjust the spray characteristics of the spray during the delivery of the unit dose from dispenser 200, and the user may so adjust the spray characteristics of the spray based upon visual observation of the spray while delivering the unit dose from dispenser 200.

As the unit dose of liquid 212 is delivered from container 280, the piston 260 moves with piston stroke $S_2$, illustrated in FIG. 8C, as piston 260 is advanced within container 280 from alignment with container 280 at operational stage 215 to biasing of at least portions of piston face 261 against surface 275 of container 280 at operational stage 217. Container 280 is cylindrical with circular cross-section having hydraulic diameter $D_2$, which is the diameter of the circular cross section, as illustrated in FIG. 8C.

Figure 9:
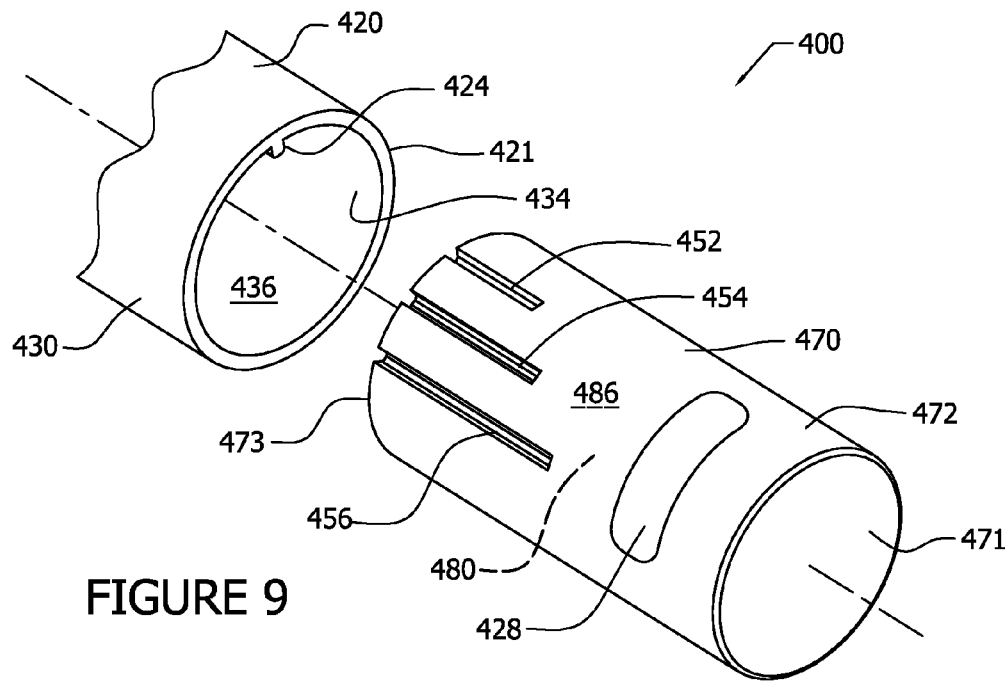
FIG. 9 illustrates by exploded perspective view portions of another exemplary implementation of a dispenser.

Portions of exemplary dispenser 400 are illustrated in FIG. 9. As illustrated in FIG. 9, body 420 of dispenser 400 forms sleeve 430. Inner surface 434 of sleeve 430 defines chamber 436, which is configured to receive container assembly 470 therein.

Container assembly 470, as illustrated in FIG. 9, includes container 480 with reservoir 486 therein. Keys 452, 454, 456 of varying lengths, as illustrated, are formed as slots (female) in outer surface 472 of container assembly 470, and configured to engage keyway 424 (male) that extends forth from surface 434 of sleeve 430 within chamber 436. Distal end 473 of container assembly 470 may be inserted through proximal end 421 of body 420 into chamber 436, and container assembly 470 may be rotated as it is inserted into chamber 436 to selectively engage keyway 424 with one of keys 452, 454, 456. The lengths of keys 452, 454, 456 limit the advancement of a piston (not shown) of dispenser 400, such as piston 60, 260, 810, 835, 855, within reservoir 486 so that the piston stroke, such as piston stroke $S_1$, $S_2$, of the piston is mechanically segmented to allow selection of the unit dose delivered by dispenser 400. The lengths of keys 452, 454, 456 may be calibrated to unit doses to be delivered from container 480, in this implementation. Accordingly, the user may select the unit dose to be delivered by selecting the corresponding key 452, 454, 456. In some implementations, the user may engage keys 452, 454, 456 successively with keyway 424 to deliver multiple unit doses from container 480. The user may push on proximal end 471 of container assembly 470, in this implementation, to engage container 480 with the piston. Container assembly 470 includes grippable surface 428 to assist the user in rotating container assembly 470 in order to engage one of keys 452, 454, 456 with keyway 424.

Figure 10:
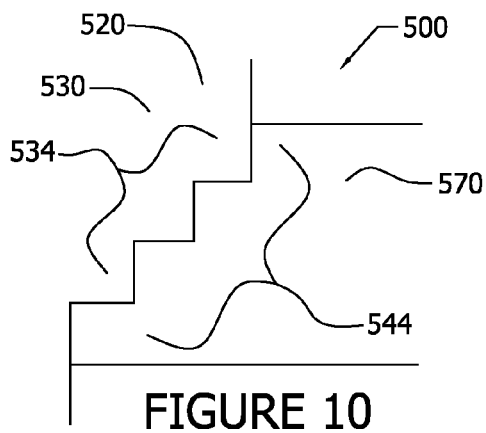
FIG. 10 illustrates by side view portions of yet another exemplary implementation of a dispenser.

FIG. 10 illustrates portions of exemplary dispenser 500. As illustrated in FIG. 10, steps 534 formed in sleeve 534 are selectively engagable with steps 544 formed in container assembly 570. The advancement of a piston of dispenser 500 within a container of container assembly 570 may be selected by selecting the engagement between steps 534 and steps 544, in this implementation. Accordingly, in this implementation, the unit dose delivered by dispenser 500 may be selected by selecting the engagement between steps 534 and steps 544, which selectively mechanically segments the piston stroke, such as piston stroke $S_1$, $S_2$, of the piston, such as piston 60, 260, 810, 835, 855, within dispenser 500.

Figure 11:
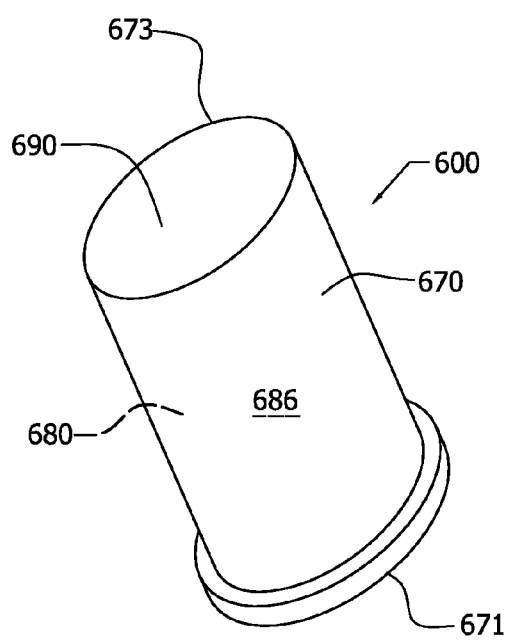
FIG. 11 illustrates by perspective view portions of another exemplary implementation of a dispenser.

FIG. 11 illustrates portions of exemplary dispenser 600 including container assembly 670. Covering 690 extends across distal end 673 of container assembly 670 to hermetically seal chamber 686 within. The user may push upon surface 671 to insert container assembly 670 and advance container assembly 670. Container assembly 670 is elliptically shaped in cross section but is cylindrical in length, in this implementation, to be received within a corresponding elliptically shaped sleeve (not shown) and to engage with a piston, such as piston 60, 260, 810, 835, 855. The piston may be elliptically shaped in correspondence to the container. The elliptical shape of container assembly 670 may orient the container assembly 670 with the corresponding sleeve and prevent rotation of the container assembly 670 within the sleeve in lieu of a key-keyway configuration. Note that container assembly 670 is devoid of a key, in this implementation. The container assembly 670 may assume various other cross-sectional shapes such as square, hexagonal, or rectangular, in other implementations. Chamber 686 may assume various cross-sectional shapes such as square, hexagonal, or rectangular, in other implementations. The cross-sectional shape of chamber 686 may either be the same as or differ from the cross-sectional shape of container assembly 670, in various implementations.

FIG. 12 illustrates portions of exemplary dispenser 700. As illustrated in FIG. 12, dispenser 700 include container 780 with proximal end 781 and distal end 783. Covering 790 is disposed about distal end 783 to hermetically seal chamber 786 within container 780. Proximal end 781 of container 780 may be inserted through distal end 763 of housing 760 into chamber 766 so that container 780 is received within housing 760. In this implementation of container assembly 770, container 780 is separable from housing 760 of container assembly 770. Accordingly, various containers 780 may be placed in housing 760, and multiple containers 780 that may contain multiple liquids may be used with housing 760. Proximal end 761 provides a surface upon which the use may push to insert container assembly 770 including container 780 into a sleeve of dispenser 700.

FIG. 13 illustrates portions of exemplary dispenser 800 including piston 810. As illustrated in FIG. 13, piston 810 includes piston side 817 and piston face 815. Inlet 825 is formed in piston face 815 for the inflow of liquid, such as liquid 12, 212, therethrough. Axis 819 passes through piston 810, as illustrated, and piston face 819 angled with respect to axis 819 such that cutting edge 828 forms angle 821 with respect to axis 819 with angle 821 being less than 90°. Cutting edge 828 thus extends forward of piston 810, in this implementation, to open the covering, such as covering 90, 290, 690, 790.

FIG. 14 illustrates portions of exemplary dispenser 830 including piston 835. As illustrated in FIG. 13, piston 835 defines piston side 837 and piston face 841. Cutting edges 838, 839, 843, 845 extend forth from piston face 841 of piston 835, as illustrated, in a cross configuration. Inlet 847 is formed at the intersection of blades 838, 839, 843, 845, in this configuration.

FIG. 15 illustrated portions of exemplary dispenser 850 including piston 855. Piston 855 defines piston side 857 and piston face 861. Inset 867 is secured within piston 855, and an oblate spheroidal portion 868 of inset 867 extends forth from piston face 861, as illustrated. Cutting edges, such as cutting edges 871, 873, 875 are formed circumferentially around oblate spheroidal portion 868 of inset 867 to open the covering, such as covering 90, 290, 690, 790, in this implementation. Inlets, such as inlets 881, 883, 885, are disposed circumferentially around piston face 861 proximate insert 867, as illustrated.

Figure 17:
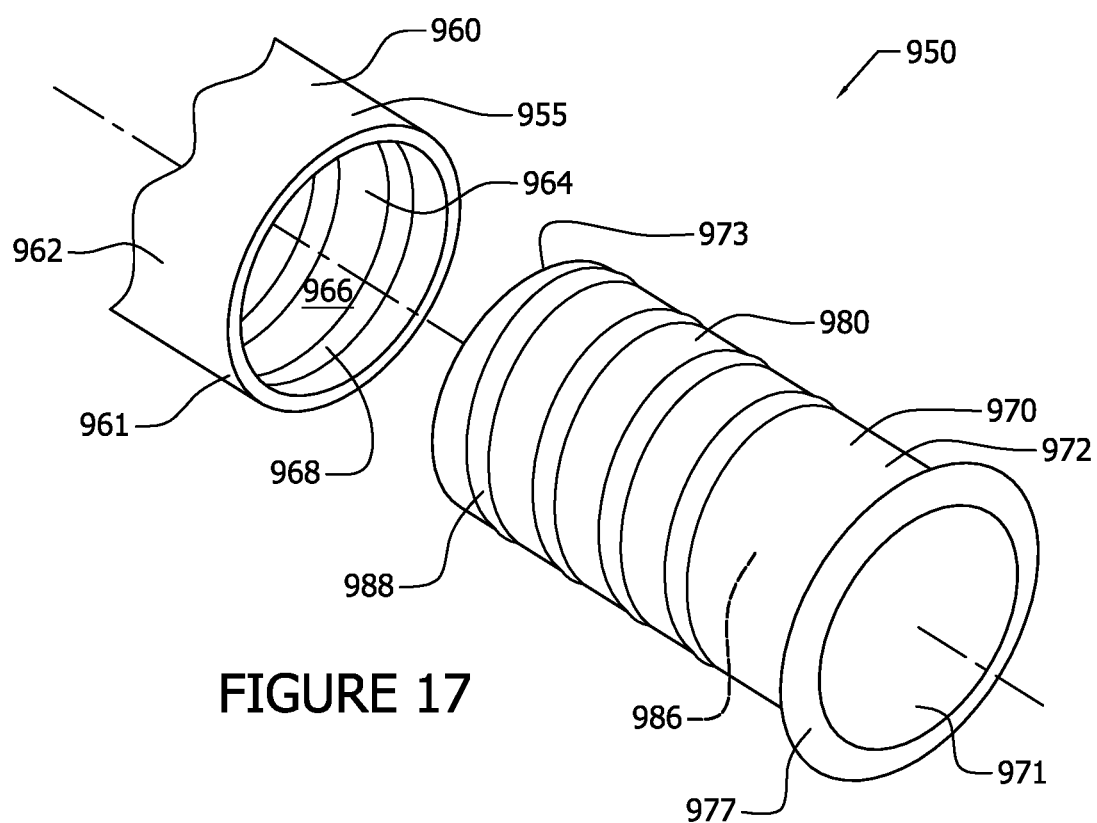

FIG. 17 illustrates portions of exemplary dispenser 950, in which container assembly 970 is threadedly engagable with body 955 to move container assembly within body 955 by rotation of container assembly 970. As illustrated in FIG. 17, body 955 of dispenser 950 forms sleeve 960. Inner surface 964 of sleeve 960 defines chamber 966, which is configured to receive container assembly 970 therein. Container assembly 970, as illustrated in FIG. 17, includes container 980 with reservoir 986 therein. Thread 988 (male), as illustrated, is formed helically around outer surface 972 of container assembly 970, and configured to engage threadedly with thread 968 (female) formed helically within surface 964 of sleeve 960 within chamber 966.

Distal end 973 of container assembly 970 may be inserted through proximal end 961 of body 950 into chamber 966, and container assembly 970 may be rotated as container assembly 970 is inserted through proximal end 961 of body 950 into chamber 966 to engage thread 988 with thread 968. With thread 988 engaged with thread 968, rotation of container assembly 970 causes the container assembly 970 to advance within chamber 966 to engage a piston (not shown), such as piston 60, 260, 810, 835, 855, within reservoir 986, to first align the piston with container 980 of the container assembly 970 and then deliver a unit dose of liquid from reservoir 986 by the sliding of the piston within reservoir 986 of the container 980. The user may rotate container assembly 970 using grippable surface 977 disposed circumferentially about proximal end 971 of container assembly 970 to advance threadedly container assembly 970 within sleeve 960 of dispenser 950. Container assembly 970 may be withdrawn from sleeve 960 by reverse rotation of container assembly 970.

The rate of advancement of the container assembly 970 within sleeve 960, and, hence, the delivery of the unit dose may be controlled by the rate of rotation of the container assembly 970 and the lead of thread 988. Thread 988 and thread 968 may have various pitches, leads, diameters, depths, left or right handedness, and other geometric properties, in various implementations. In some implementations, thread 968 may be male and thread 988 may be female.

FIG. 16 illustrates exemplary method 900 of dispensing a unit dose of liquid, such as liquid 12, 12, from a dispenser, such as dispenser 10, 200, 400, 500, 600, 700, 800, 830, 850, 950 as spray, such as spray 14. Method 900 is entered at step 901. At step 905, the user inserts a container assembly, such as container assembly 70, 270, 470, 570, 670, 770, 970 into a sleeve, such as sleeve 30, 230, 430, 530, 960. In some implementations, a key, such as key 74, 274, 452, 454, 456, disposed about the container assembly may be engaged with a keyway, such as keyway 24, 224, 424, disposed about the sleeve as the container assembly is inserted into the sleeve. In some implementations, a thread, such as thread 968, disposed about the sleeve may be threadedly engaged with a thread, such as thread 988, disposed about the container assembly.

At step 910, in implementations with slidable engagement between the sleeve and the container assembly, the user presses upon portions of the dispenser, such as arms 27, 29, and presses upon portions of the container assembly, such as proximal end 71, 271, 471, 671, 761, thereby causing the container assembly to slide within the sleeve. With the user so pressing, a cutting edge, such as cutting edge 68, 268, 828, 838, 839, 843, 868, formed about a piston, such as piston 60, 260, 810, 835, 855, opens covering, such as covering 90, 290, 690, 790, that hermetically seals container, such as container 80, 280, 480, 680, 780, per step 910.

Alternatively, at step 910, in implementations with threaded engagement between the container assembly and the sleeve, the user may rotate the container assembly, which is threadedly engaged with the sleeve, causing the container assembly to advance within the sleeve. As the container assembly advances within the sleeve, the cutting edge formed about the piston opens the covering that seals the container, at step 910.

In implementations with slidable engagement between the sleeve and the container assembly, continued pressing upon the dispenser by the user causes the piston to align with the reservoir, such as reservoir 86, 286, 486, 686, 786, 986 of the container, at step 915. Alternatively, in implementations with threaded engagement between the container assembly and the sleeve, continued rotation of the container assembly causes the piston to align with the reservoir, at step 915. Upon alignment at step 915, the displaced volume, such as displaced volume 88, 288, is less than or equal to the priming volume, such as priming volume 59, 259.

In implementations with slidable engagement between the sleeve and the container assembly, the user may then press upon the dispenser to dispense a unit dose of liquid from the container as spray at step 920. The piston advances through the reservoir until the piston face, such as piston face 61, 261, 815, 841, 861 strikes a surface, such as surface 75, 275, of the container, which thereby limits the advance of the piston within the reservoir. In implementations with threaded engagement between the container assembly and the sleeve, continued rotation of the container assembly causes the piston to advance within the reservoir thereby delivering the unit dose of liquid, at step 920.

The foregoing discussion along with the Figures discloses and describes various exemplary implementations. These implementations are not meant to limit the scope of coverage, but, instead, to assist in understanding the context of the language used in this specification and in the claims. Upon study of this disclosure and the exemplary implementations herein, one of ordinary skill in the art may readily recognize that various changes, modifications and variations can be made thereto without departing from the spirit and scope of the inventions as defined in the following claims.

The invention claimed is:

1. An apparatus, comprising:
a container that defines a distal end sealingly secured to a cover and a proximal end enclosed fixedly by a proximal surface, the container contains a liquid, the container engageable with a dispenser, the distal end being most distal with respect to the dispenser and the proximal end being most proximal with respect to the dispenser when the container is engaged with the dispenser, the dispenser comprising a piston having a piston face slidably positionable from the distal end into contact with the proximal surface of the container to expel the liquid distally through a passage entered through the piston face.

2. The apparatus of claim 1, further comprising:
a container assembly comprising the container, the container engageable with the dispenser by engagement of the container assembly with the dispenser.

3. The apparatus of claim 2, wherein the container is separable from the container assembly to allow replacement of the container within the container assembly.

4. The apparatus of claim 2, comprising:
a sleeve surrounding the piston configured to engage the container assembly as the piston is inserted into the container;
a key configured about the container assembly; and
a keyway configured about the sleeve to cooperate with the key.

5. A dispenser apparatus, comprising:
a container that defines a distal end located most distally with respect to said dispenser and a proximal end located most proximally with respect to said dispenser, a proximal surface encloses fixedly the proximal end of the container and a cover is sealingly secured to the distal end of the container and the container contains a liquid; and
said dispenser comprises a piston slideably sealingly engageable within the container to advance a piston face of the piston from the distal end of the container into contact with the proximal surface of the container in order to expel the liquid distally through a passage entered through the piston face.

6. The apparatus of claim 5, further comprising:
a displaced volume defined by the piston when the piston is aligned with the container; and
a priming volume defined by the passage, the priming volume at least equal to the displaced volume.

7. The apparatus of claim 5, further comprising:
a cutting edge disposed on the piston face to open the cover as the piston is advanced toward the proximal end.

8. The apparatus of claim 5, further comprising:
a shoulder formed circumferentially about a periphery of the piston face to align the piston within the container as the shoulder strikes a distal end of the container.

9. The apparatus of claim 8, wherein the shoulder is configured to form at least a portion of a cutting edge to open the cover.

10. The apparatus of claim 5, further comprising:
a nozzle comprising a nozzle exit in fluid communication with the passage to emit the liquid as the piston is advanced toward the proximal end.

11. The apparatus of claim 10, wherein the droplet size of droplets spayed from the nozzle is generally within a range of from about 100 microns to about 300 microns.

12. The apparatus of claim 5, further comprising:
a swirl chamber in fluid communication with the passage.

13. The apparatus of claim 5, further comprising:
a plurality of passages in fluid communication with the piston face.

14. The apparatus of claim 5, wherein a piston stroke S of the piston with respect to a hydraulic diameter D of the container is defined by the relationship $S/D \geq 1$.

15. The apparatus of claim 5, further comprising:
a piston stroke of the piston is mechanically segmented to allow selection of a unit dose delivered by said dispenser.

16. The apparatus of claim 5, further comprising:
the container is operably received by the dispenser.

* * * * *